United States Patent
Zuidema et al.

(10) Patent No.: US 11,673,847 B2
(45) Date of Patent: Jun. 13, 2023

(54) ISOMERISATION PROCESS

(71) Applicant: SHELL OIL COMPANY, Houston, TX (US)

(72) Inventors: Erik Zuidema, Amsterdam (NL); Donald Paul Church, Amsterdam (NL); Daniël Banen, Amsterdam (NL); Henriette Siegers, Amsterdam (NL)

(73) Assignee: SHELL USA, INC., Houston, TX (US)

( * ) Notice: Subject to any disclaimer, the term of this patent is extended or adjusted under 35 U.S.C. 154(b) by 0 days.

(21) Appl. No.: 17/416,229

(22) PCT Filed: Dec. 19, 2019

(86) PCT No.: PCT/EP2019/086483
§ 371 (c)(1),
(2) Date: Jun. 18, 2021

(87) PCT Pub. No.: WO2020/127847
PCT Pub. Date: Jun. 25, 2020

(65) Prior Publication Data
US 2022/0048835 A1  Feb. 17, 2022

(30) Foreign Application Priority Data
Dec. 21, 2018  (EP) ................... 18215417

(51) Int. Cl.
*C07C 5/27* (2006.01)
*B01J 35/02* (2006.01)
(Continued)

(52) U.S. Cl.
CPC ......... *C07C 5/2775* (2013.01); *B01J 35/026* (2013.01); *B01J 37/0009* (2013.01);
(Continued)

(58) Field of Classification Search
None
See application file for complete search history.

(56) References Cited

U.S. PATENT DOCUMENTS

| 3,140,249 A | 7/1964 | Plank et al. |
| 3,140,251 A | 7/1964 | Plank et al. |

(Continued)

FOREIGN PATENT DOCUMENTS

| WO | 2004074221 A1 | 9/2004 |
| WO | 2004094349 A1 | 11/2004 |

(Continued)

OTHER PUBLICATIONS

Rault et al. "The Future Role of Aromatics in Refining and Petrochemistry", Proceedings of the DMGK-Conference, Oct. 13-15, 1999, pp. 131-138. (Year: 1999).*

(Continued)

*Primary Examiner* — Philip Y Louie
*Assistant Examiner* — Alyssa L Cepluch
(74) *Attorney, Agent, or Firm* — Shell USA, Inc.

(57) ABSTRACT

The invention relates to a process for combined ethylbenzene reforming and xylene isomerisation comprising contacting a hydrocarbon feedstock containing ethylbenzene and xylene with a catalyst comprising a catalyst carrier and one or more metal(s) supported on the catalyst carrier, wherein the catalyst carrier is an extrudate comprising (i) a ZSM-48 and/or EU-2 type zeolite and (ii) an alumina binder, the extrudate having a shape with a C/A value of at least 3, where C is the circumference of the extrudate and A is the cross-sectional area of the extrudate. The metal may be platinum and the alumina may be a wide-pore alumina. The process displays high conversion rates whilst maintaining low levels of side-product formation.

9 Claims, 1 Drawing Sheet (a)     (b)

(c)     (d)

(51) Int. Cl.
*B01J 37/00* (2006.01)
*B01J 29/74* (2006.01)

(52) U.S. Cl.
CPC ......... *C07C 5/2737* (2013.01); *B01J 29/7461* (2013.01); *C07C 2529/74* (2013.01)

(56) References Cited

U.S. PATENT DOCUMENTS

| | | | |
|---|---|---|---|
| 3,140,253 | A | 7/1964 | Plank et al. |
| 3,856,872 | A | 12/1974 | Morrison |
| 4,741,891 | A | 5/1988 | Casci et al. |
| 5,028,573 | A | 7/1991 | Brown et al. |
| 5,075,269 | A | 12/1991 | Degnan et al. |
| 2004/0214713 | A1 | 10/2004 | Buchanan et al. |
| 2014/0179969 | A1* | 6/2014 | Nenu .................. B01J 37/0213 585/481 |
| 2014/0378697 | A1 | 12/2014 | De Smit et al. |
| 2016/0228861 | A1 | 8/2016 | Lai et al. |

FOREIGN PATENT DOCUMENTS

| | | |
|---|---|---|
| WO | 2011100218 A1 | 8/2011 |
| WO | 2012055755 A1 | 5/2012 |

OTHER PUBLICATIONS

Alario et al. Para-xylene Manufacturing: Catalytic Reactions and Processes in "Zeolites for Cleaner Technologies", Imperial College Press, 2002, pp. 189-207. (Year: 2002).*
Guillon et al. How to Improve the Selectivity of Zeolitic Catalysts in C8 Aromatic Cut Isomerization, Oil & Gas Science and Technology, Rev. IFP, vol. 64 (2009), No. 6, pp. 731-744. (Year: 2009).*
Dorsey et al. "Xylene-loop scheme for minimized GHG emissions and PX production cost", HydrocarbonProcessing.com, Jun. 2022, pp. 21-25. (Year: 2022).*
International Search Report and Written Opinion received for PCT Patent Application No. PCT/EP2019/086483, dated Feb. 28, 2020, 10 pages.
Zhang et al., "Dealuminated Zeolite-based Composite Catalysts for Reforming of an Industrial Naphthene-rich Feedstock", Applied Catalysis, vol. 168, Issue No. 1, Mar. 1998, pp. 113-130.
Olson et al., "Atlas of Zeolite Framework Types", 5th Revised Edition, 2001, 308 pages.
Database of Zeolite Structures, Catalog of Disorder in Zeolite Frameworks, 2000, 3 pages.

* cited by examiner

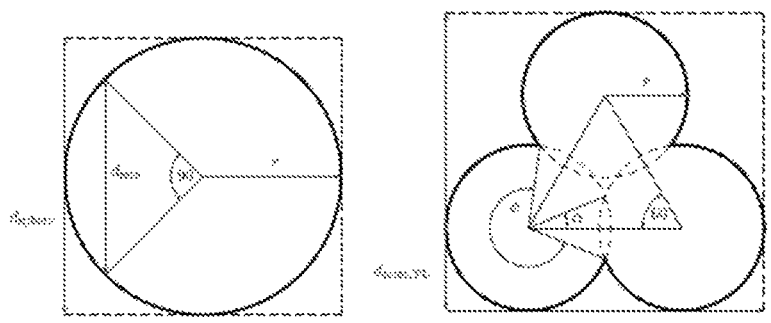
(a)　　　　　　　　(b)
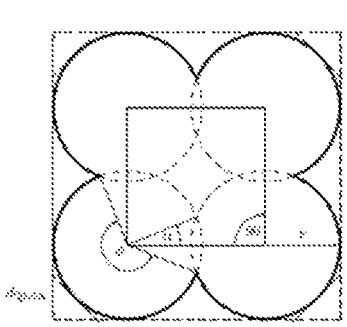　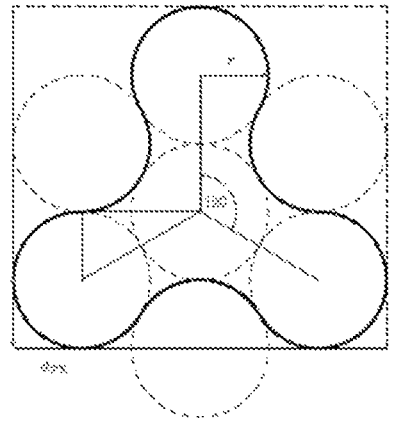
(c)　　　　　　　　(d)

ISOMERISATION PROCESS

CROSS REFERENCE TO RELATED APPLICATIONS

This is a National stage application of International application No. PCT/EP2019/086483 filed 19 Dec. 2019, which claims priority of European application No. 18215417.9, filed 21 Dec. 2018, which is incorporated herein by reference in its entirety.

FIELD OF THE INVENTION

The present invention relates to a process for ethylbenzene reforming and isomerising xylenes using a zeolite-based catalyst.

BACKGROUND OF THE INVENTION

Following fractionation or distillation of crude petroleum oil, a straight-run naphtha fraction, boiling in the 70° C. to 190° C. range, is obtained. This fraction may be catalytically converted to an aromatic reformate.

On conversion to reformate, the aromatics content is considerably increased and the resulting hydrocarbon mixture becomes highly desirable as a source of valuable chemical intermediates and as a component for gasoline.

Reformate generally contains aromatic hydrocarbons having 8 carbon atoms such as ethylbenzene and xylenes. Other components may be present such as their hydrogenated homologues such as naphthenes.

Within the xylenes, para-xylene is the most useful commodity and isomerisation or transalkylation processes have been developed to increase the proportion of para-xylene ("pX"). However, isomerisation or transalkylation processes can also produce undesired side-products such as compounds having from 1 to 5 carbon atoms, benzene, toluene, and compounds having 9 or more carbon atoms.

Many catalysts have been made and proposed for various reactions involving aromatics, but for some reactions, such as ethylbenzene isomerisation or transalkylation processes, there is commonly a trade-off between providing the desired products and known side reactions. One common side reaction of ethylbenzene hydroisomerisation is the formation of compounds having from 1 to 5 carbon atoms, which is disadvantageous from an environmental and economical point of view.

U.S. Pat. No. 3,856,872 A describes a xylene isomerization process in which a conventional platinum on silica-alumina catalyst is replaced by a zeolite catalyst of the ZSM-5 type, or a zeolite ZSM-12 catalyst or a zeolite ZSM-21 catalyst. The zeolite can be incorporated in an inert alumina matrix.

The article "Dealuminated zeolite-based composite catalysts for reforming of an industrial naphthene-rich feedstock" (Applied Catalysis, Volume 168, Issue 1, March 1998, pp 113-130) describes reforming catalysts for naphthenic feedstocks. The preferred ZSM-12 zeolite has a Si/Al ratio of 54. It is taught that ZSM-12 having higher silica to alumina ratios should not be used for such catalysts as this produces large amounts of CH4 and less aromatics.

Other catalysts known for use in C8 aromatic isomerization processes include those based on mordenite (MOR) and EU1 (EUO) zeolites as defined in the Atlas of Zeolite Framework Types, Olson et al, 5th revised edition, 2001, published on behalf of the Structure Commission of the International Zeolite Association, by Elsevier. EU1-based catalysts can achieve high selectivity, but this is typically accompanied by low ethylbenzene conversion rates, therefore limiting throughput. MOR and ZSM-12 based catalysts tend to achieve higher ethylbenzene conversion rates, but they also produce more side-products in the form of toluene and C9+ aromatics.

From U.S. Pat. Nos. 4,741,891 A and 5,075,269, it is known that ZSM-48 and/or EU-2 zeolite are suitable for use in hydrocarbon conversion catalysts. As described in the "Catalog of Disorder in Zeolite Frameworks" published in 2000, both ZSM-48 and EU-2 zeolite belong to the family of MRE-type zeolites.

WO 2012/055755 A1 describes dealuminated ZSM-48 and/or EU-2 zeolites with a refractory oxide essentially free of alumina for use as hydrocarbon conversion catalysts.

An object of the present invention is to provide an improved process for reforming of alkylaromatics, especially C8 alkylaromatics such as ethylbenzene, and isomerisation of xylenes.

SUMMARY OF THE INVENTION

It has unexpectedly been found that this object can be realized when use is made of a catalyst system comprising a ZSM-48 and/or EU-2 zeolite, especially a shaped catalyst system of ZSM-48 and/or EU-2 zeolite in which the circumference of the shaped catalyst is enhanced in relation to its cross-sectional area.

Accordingly, the present invention provides a process for combined ethylbenzene reforming and xylene isomerisation comprising contacting a hydrocarbon feedstock containing ethylbenzene and xylene with a catalyst comprising a catalyst carrier and one or more metal(s) supported on the catalyst carrier, wherein the catalyst carrier is an extrudate comprising (i) a ZSM-48 and/or EU-2 type zeolite and (ii) an alumina binder, the extrudate having a shape with a C/A value of at least 3, where C is the circumference of the extrudate and A is the cross-sectional area of the extrudate.

DETAILED DESCRIPTION OF THE INVENTION

In the present invention, the use of the aforementioned shaped catalyst carrier extrudate has been found to be surprisingly beneficial in providing a catalyst for the isomerisation of alkylaromatics containing 8 carbon atoms. Moreover, the shaped catalyst used in the process of the invention is able to: reduce side reactions such as formation of compounds containing from 1 to 5 carbon atoms, and/or; reduce formation of benzene, and/or; increase the conversion of ethylbenzene; and/or increase the production of other desired products such as para-xylene.

One of more of the above provisions leads to an increase in the final yield of one or more of the desired products, and unexpectedly leads to high pX-approach to equilibrium ("pX-ATE") values whilst maintaining excellent ethylbenzene conversion.

In the present invention, the reference to ZSM-48 and EU-2 is used to indicate that all zeolites can be used that belong to the MRE family of disordered structures as described in the "Catalog of Disorder in Zeolite Frameworks" published in 2000 on behalf of the Structure Commission of the International Zeolite Association. Zeolites ZBM-30 and EU-11 closely resemble ZSM-48 and are also considered to be members of the zeolites whose structure belongs to the MRE family. Thus, in the present application, any reference to ZSM-48 zeolite also is a reference to EU-2, ZBM-30 and EU-11 zeolite.

The silica to alumina molar ratio of the ZSM-48 and/or EU-2 zeolite may influence the properties of the catalyst derived from it. The silica to alumina molar ratio ("SAR") is to be determined by bulk ratio. This ratio is also referred to as the overall ratio. Such ratio is different from the SAR of the crystalline framework. The bulk or overall ratio can be determined by any one of a number of chemical analysis techniques. Such techniques include X-ray fluorescence, atomic adsorption, and inductive coupled plasma-atomic emission spectroscopy (ICP-AES). All will provide substantially the same bulk ratio value. The silica to alumina molar ratio for use in the present invention is determined by X-ray fluorescence.

The SAR of the ZSM-48 and/or EU-2 zeolite preferably is at least 50, more specifically at least 70, more specifically at least 100, most preferably at least 110. The SAR of the ZSM-48 and/or EU-2 zeolite preferably is at most 300, more specifically at most 250, more specifically at most 200, most specifically at most 160.

The ZSM-48 and/or EU-2 zeolite can be prepared in any way known to a person skilled in the art. U.S. Pat. Nos. 5,075,269 and 4,741,891 describe suitable manufacturing methods for such zeolites having a SAR of from 100 to 250.

The ZSM-48 and/or EU-2 zeolite may be dealuminated. Dealumination may be attained by methods known in the art, such as for example acid leaching or by a steam treatment. Steam treatment is effected by contacting the zeolite, preferably as part of a catalyst composition, with steam at elevated temperatures ranging from about 250° C. to 650° C. and preferably from about 400° C. to 550° C. The treatment can be accomplished in an atmosphere of 100% steam or in an atmosphere consisting of steam or some other gas which is essentially inert to the zeolites. A similar treatment can be accomplished at lower temperatures and elevated pressure, e.g., from 180° C. to 370° C. at from 10 to 200 atmospheres.

The expression "dealumination" is used to indicate that aluminium and/or aluminium containing compounds such as alumina are removed from the bulk of the zeolite. The aluminium and aluminium containing compounds can but do not need to be part of the zeolite framework.

The ZSM-48 and/or EU-2 zeolite is combined with an alumina binder in the catalyst carrier of the invention. In an embodiment, the alumina binder preferably comprises a "wide-pore alumina", sometimes referred to alternatively as "high pore" alumina. By "wide-pore alumina" is meant that the average pore diameter of the alumina is about 80 Å or greater, preferably greater than about 90 Å. In a further embodiment, the wide-pore alumina may have a surface area greater than about 200 m$^2$/g and about 25% or more of its pores are greater than about 350 Å in diameter.

Said wide-pore alumina may have a pore volume of at least about 0.5 cm$^3$/g, preferably at least 0.6 cm$^3$/g, and more preferably at least 1.2 cm$^3$/g. The pore volume may be up to about 2.0 cm$^3$/g, preferably up to 1.6 cm$^3$/g.

It is believed that the more open structure of a wide-pore alumina, based upon one or more parameters such as pore volume, pore diameter and bulk density, provide better diffusion of the reactant(s) reaching the catalytic material in the catalyst, and better diffusion of the product(s) away from the catalytic material.

Examples of wide-pore aluminas suitable for use in the catalyst of the invention include grades of the Pural range from Sasol, such as "Pural KR II" (average bulk density of 0.315 g/cm$^3$, pore volume of 1.4 cm$^3$/g, and average surface area of 290 m$^2$/g) and other wide-pore aluminas, such as WPA available from Criterion (average bulk density of 0.2 g/cm$^3$, pore volume of 1 cm$^3$/g, and average surface area of 345 m$^2$/g). Pore size and pore volume may be measured by mercury intrusion porosimetry testing (MIP).

When the content of binder and zeolite is stated in the context of the present invention, the content on a dry basis is meant. The catalyst composition for use in the process of the present invention preferably comprises at most 80% by weight (% wt) of zeolite, more specifically at most 70% wt, more specifically at most 65% wt, most preferably at most 55% wt. These amounts preferably apply to the ZSM-48 and/or EU-2 zeolite. Further, it is preferred that the amount of ZSM-48 and/or EU-2 zeolite is at least 30% wt, more specifically at least 35% wt, more specifically at least 40% wt, most specifically at least 45% wt.

Optionally, besides ZSM-48 and/or EU-2 zeolite, further zeolites may be present in the catalyst composition, especially if it is desired to modify its catalytic properties. If further zeolite is present besides the ZSM-48 and/or EU-2 zeolite, such zeolite preferably is present in an amount of at most 50% wt, based on amount of ZSM-48 and EU-2 zeolite which is present.

The combined alkylaromatics reforming and xylene isomerization catalyst for use in the process of the present invention may be prepared by extruding a mixture comprising a ZSM-48 and/or EU-2 type zeolite and alumina to form a catalyst carrier having a C/A value of at least 3, and impregnating the extruded catalyst carrier with a metal.

The catalyst carrier may be extruded prior to loading with metal. Preferably the catalyst carrier is calcined before metal loading. Calcining may take place at from 350-850° C., more preferably at from 400-750° C. in an inert atmosphere or in an oxygen-containing gas.

The catalyst carrier is shaped or formed by extrusion, such as by preparing an extrudable mass comprising alumina binder and ZSM-48 and/or EU-2 zeolite. This extrudable mass may have a viscosity that permits extrusion into shapes, preferably the viscosity being such that the extruded shapes are maintained during subsequent calcining. One skilled in the art will know how to achieve an extrudable mixture, such as a paste like mixture, which is susceptible to such extrusion and retention of the extruded shape thereafter while calcining. For example, the extrudable mass preferably has a water content that is sufficient to provide for extrusion whilst retaining the extruded shape during subsequent calcination. Preferably the water content does not exceed 65%, and preferably is at least 35% by weight.

The zeolite and alumina mixture may further comprise a peptizing agent to change the pH of the mixture sufficiently to induce de-agglomeration of the solid particles. Peptizing agents are well-known and encompass inorganic acids, such as sulphuric acid or nitric acid, as well as organic acids, such as formic acid and acetic acid. Such peptizing agents are removed upon calcination.

A plasticising agent may be added to the catalyst carrier composition, preferably the plasticising agent is introduced before extrusion. The plasticising agent may be used to increase the viscosity of the mixture in order to obtain an extrudable mass. Suitable plasticising agents are for example dextrose, gelatine, glucose, glues, gums, salts, waxes, starch and cellulose ethers. Methylcellulose and/or methylcellulose derivatives are especially suited as organic binders in the practice of the present invention with methylcellulose, hydroxypropyl methylcellulose, or combinations of these being preferred. Preferred sources of cellulose ethers are "Methocel" A4M, F4M, F240, and K75M from Dow Chemical Co.

Extrusion of the catalyst carrier composition may be performed by any of the well-known extrusion processes. Examples of such methods are extrusion performed by a screw extruder, or a plate or ram extruder.

The extrudates can have a variety of forms and sizes, subject to having a C/A value of at least 3, wherein C is the circumference and A is the cross-sectional area of the extrudate. Note that the cross-sectional area (A) of the extrudate is measured a right angles (perpendicular) to the extrusion axis, and the circumference (C) thereof is the length of the perimeter of the extrudate around the cross-section. The extrudates having a C/A value of at least 3 may conveniently be formed as cylindrical or multi-lobe extrudates, for example, having trilobe, quadralobe or extended trilobe shapes. That is to say, in the present invention, in cross-section, the catalyst carrier preferably has a circular, trilobe, quadralobe or extended trilobe shape. More preferably, in cross-section, the catalyst carrier has a trilobe, quadralobe or extended trilobe shape.

The extrudable composition comprising the ZSM-48 and/or EU-2 zeolite and alumina binder may be extruded using extruder die-plates provided with apertures that produce an extrudate having the required cross-section to achieve a C/A value of at least 3.

After extrusion, the extrudates obtained are preferably subjected to drying prior to calcining. Drying preferably takes place at a temperature of from 60° C. to 250° C., for a time sufficient to dry the extrudate, for example, for at least 1 hour. Calcining preferably takes place in an oxygen containing gas, including in air, or in an inert gas, at temperatures ranging from 250° C. to 850° C. for periods of time ranging, for example, from 1 to 48 hours or more.

The extruded catalyst carriers may be divided, such a cut or broken, preferably after the initial calcining step, to reduce their length to diameter ratio and thereby assist in reducing breakage of the catalyst, for example when subjected to crushing forces in the catalyst bed of a reactor. The length to diameter ratio may optionally range from 1:1 to 20:1, preferably from 2:1 to 9:1, most preferably from 4:1 to 8:1. For example, the diameter of the extruded catalyst may be in the range of from 0.5 to 5 mm, preferably from 1 to 2 mm, and the average length of the catalyst shapes may be in the range of from 2 to 10 mm, preferably from 4 to 9 mm, more preferably about 8 mm.

The catalyst further comprises one or more metals, preferably incorporated into the catalyst carrier. The metal may be incorporated by means of impregnation of the zeolite, by impregnation of the alumina support, or by impregnation of the composite of the zeolite and support. Preferably the metal is incorporated into the catalyst carrier. Incorporation of the metal may be performed using ion-exchange techniques, such as involving contacting the catalyst carrier composition with a salt of the desired metal ion. This can be done by for example pore volume impregnation or continuous solution impregnation. Representative ion-exchange techniques are disclosed in a wide variety of patent specifications including U.S. Pat. Nos. 3,140,249 A, 3,140,251 A and 3,140,253 A.

The catalytic metal(s) are preferably incorporated by pore volume impregnation. More preferably, the metal(s) are incorporated by impregnation into the extruded catalyst carrier, for example, following calcination of the carrier. Most preferably, impregnation is carried out after both calcination and division of the extruded carrier into the desired length(s).

The catalytic metal(s) are selected from the group consisting of metals of Group VIII of the Periodic Table of the Elements as shown in the Handbook of Chemistry and Physics, 63$^{rd}$ edition 1983, more specifically selected from one or more of platinum, palladium, cobalt, iron, and nickel. Preferably, the one or more catalytic metals are chosen from the group consisting of platinum, palladium and nickel, with platinum being especially preferred. Combinations of two or more catalytically active metals are also possible, preferably being platinum metal combinations. The catalytically active metal may be provided in the form of a compound, optionally requiring activation prior to use.

The catalytic metal may be included in the final catalyst composition in an amount of up to about 3 wt % based upon the total dry weight of the catalyst, the metal content being determined as an element, regardless of its actual form. It is preferred that the metal component be present in the catalyst composition in an amount of from 0.1 wt % to 3 wt %. More preferably, the metal is present in the composition in an amount of from 0.2 to 2 wt %, and most preferably, it is in the range of from 0.3 to 1 wt %. More preferably, the catalyst composition comprises about 0.3 wt % platinum.

The catalyst finds utility in isomerization and reforming processes, especially ethylbenzene conversion and xylene isomerization as described herein.

Advantageously, catalysts prepared as hereinbefore described can be used in alkylaromatics isomerisation for preparing a product of increased xylene content.

The catalysts described herein are especially suitable for use in increasing the xylenes content, more specifically the para-xylene content, of a hydrocarbon fraction containing aromatic hydrocarbons having 8 carbon atoms. The hydrocarbon stream preferably contains at most 60 wt % of ethylbenzene, more specifically at most 50% wt. Preferably, the hydrocarbon stream comprises at least 8% wt, more specifically at least 10% wt, most preferably at least 15 wt % of ethylbenzene. The hydrocarbon stream preferably is contacted with the catalyst at a temperature in the range of from 300 to 450° C., preferably at least 340° C. and preferably at most 400° C.

In the process of the present invention, it has surprisingly been found that in addition to successful ethylbenzene conversion rates, further improvements in isomerisation to high para-xylene reformate, as evidenced by pX-ate values, are achieved. pX-ate (para-Xylene-approach-to-equilibrium) provides a measure of the effectiveness of the catalyst to increase the para-xylene concentration relative to the maximum achievable para-xylene concentration based on a thermodynamic equilibrium mixture of xylenes, as defined by the equation:

$$pX\text{-ate }(\%) = pX \text{ in } Xyl_{pr.} - pX \text{ in } Xyl_{f.}$$

pX in $Xyl_{eq.}$ – pX in $Xyl_{f.}$ where pX stands for para-xylene, Xyl for xylenes in general, f. for feed, and pr. for product.

In particular, it is surprising that by means of the present invention pX-ate values approaching or in excess of 100% may be achieved whilst maintaining low levels of side product formation.

Examples of catalyst shapes having a C/A value of at least 3 are shown in cross-section as FIGS. 1 (b), (c) and (d) together with a cylindrical shape as FIG. 1 (a) for comparison. It has been found that catalysts of the present invention comprising extrudates having trilobe (TL), quadralobe (QLSA) or trilobe extra (TX) cross-sections exhibit improved performance, for example, in comparison with conventional cylindrical (CYL) extrudates having a circular cross-section and C/A value of less than 3. A similar improvement is observed for cylinders with smaller diameters, which also have C/A values of above 3. On the other hand, large TX shaped extrudates, with a C/A value below 3 does not show the advantage.

C/A values of 3 or more may be achieved, for example, by extruding the catalyst through a die provided with an orifice having an undulating perimeter. In a preferred embodiment the shaped catalyst of the invention has a solid structure, for example as formed by extrusion through a solid die rather than through a hollow die that produces hollow or semi-hollow shapes.

The C/A ratio for the various catalyst shapes (a) to (d) of FIG. 1 may be determined from measurement of the radius r as indicated in the cross-sectional drawings and the circumference (C) represented by the bold lines in said drawings as calculated according to the following formulae:

| Shape | Area | Circumference |
| --- | --- | --- |
| CYL (a) | $\pi r^2$ | $2\pi r$ |
| TL (b) | $3\left[r^2\pi\dfrac{300-2\alpha}{360} + r^2\cos\alpha\sin\alpha\right] + 2r^2\cos\alpha^2\sin 60$ | $r\pi\dfrac{150-\alpha}{30}$ |
| QLI (c) | $4r^2\left[(\cos\alpha)^2 + \pi\dfrac{270-2\alpha}{360} + \cos\alpha\sin\alpha\right]$ | $8\pi r\dfrac{360-90-2\alpha}{360}$ |
| TX (d) | $\pi r^2 + 6r^2\sqrt{3}$ | $3 * 2\pi r$ |

Preferably, the catalyst is formed, such as by extrusion, into shapes having a length to diameter ratio of from 1:1 to 20:1, preferably from 2:1 to 9:1, most preferably from 4:1 to 8:1. Preferably, the diameter (d) is in the range of from about 0.5 mm to about 5 mm, more preferably from 1 mm to 2 mm. The shapes preferably have an average length (measured along the extrusion axis) of from about 2 mm to about 10 mm, more preferably from about 4 mm to about 9 mm, most preferably about 8 mm.

The catalysts as hereinbefore described may be used in a combined ethylbenzene reforming and xylene isomerisation reaction, which reaction is performed in the gas phase. Accordingly, the present invention provides a process for combined ethylbenzene reforming and xylene isomerisation comprising contacting a hydrocarbon feedstock containing ethylbenzene and xylene with a catalyst as hereinbefore described at an elevated temperature, preferably from 340-450° C. and a pressure of from 4-12 barg. Preferably, the reforming and isomerization reaction is performed using a feed weight hourly space velocity (WHSV) (weight of feed per hour/weight of catalyst) in the range of from about 1 to 20 $h^{-1}$, more preferably from about 3 to 10 $h^{-1}$. The WHSV is based upon the weight of the catalyst composition, i.e. total weight of active catalyst and binder.

Preferably the isomerization reaction is effected in the presence of hydrogen. More preferably, hydrogen may be present in the isomerization reaction zone in an amount between about 0 and about 10 mols, especially between about 1 and about 5 mols, of hydrogen per mole of hydrocarbon feedstock. The reaction may take place in the vapour, liquid or mixed phase.

One advantage of the process of the present invention is the fact that a high weight hourly space velocity can be applied in the process, resulting in a much higher throughput in the reactor and thus a higher production rates. The weight hourly space velocity applied in the process is suitably in the range of from 3-12 $hr^{-1}$.

The present invention will now be illustrated by the following non-limiting examples.

EXAMPLES

Example 1

A catalyst was prepared by the steps of: catalyst carrier extrusion, carrier calcination, platinum impregnation and final calcination.

In particular, an extrudable mixture of 78 g of EU-2 zeolite with a silica-to-alumina ratio of 110 (prepared as described in U.S. Pat. No. 4,741,891 A), 64 g of a wide-pore alumina from Criterion, 86 g of water and 2.77 g of 65% $HNO_3$ was freshly prepared and shaped by extrusion using extruder die-plates with differently shaped holes of dimensions as described in Table 1.

The resulting extruded catalyst carriers were each calcined at 600° C. for 2 h in a static oven, and then broken to an average length of 6 mm. Subsequently, the calcined carriers were impregnated with platinum by pore-volume impregnation using a mixture of chloroplatinic acid in 0.5 M aqueous $HNO_3$ solution, dried at 120° C. for 2 hours, and then calcined at 550° C. for 2 h to generate the final catalysts which contained 0.3 wt % platinum.

Example 2

Catalysts prepared by the process of Example 1 were then used in an ethylbenzene reforming process.

In particular, the catalysts were evaluated in a pilot plant for the combined ethylbenzene reforming and xylene isomerization reaction, using on-line GC analysis.

A hydrogen: hydrocarbon molar ratio of 4 was maintained throughout the reaction. Prior to the conducting the reforming process, the catalysts were dried in a flow of hydrogen at room temperature and atmospheric pressure for 1 h, then heated to 400° C. for 4 h, pressurized to 12 barg, and maintained under these conditions for a further 1 h.

A first hydrocarbon feed consisting of 20 wt % ethylbenzene and 80 wt % m-Xylene was introduced at a WHSV of 5 $h^{-1}$, and the temperature was increased to 420° C. These conditions were maintained for 24 h, before decreasing temperature to 375° C. At this temperature, the hydrocarbon feed was switched to a mixture of 20% ethylbenzene, 23% o-xylene and 57% m-xylene, at a WHSV of 4.0 $h^{-1}$. These conditions were maintained for 6 hours.

Subsequently, the reactor temperature was increased to 387° C., and the hydrocarbon feed was switched to a final mixture of 19% ethylbenzene, 15.5% o-xylene, 59% m-xylene and 6.5% ethylcyclohexane, a representative of the C8-naphthenes that mediate the ethylbenzene-reforming reaction, at a WHSV of 3.5 $h^{-1}$.

Pressure was adjusted so that the level of C8-naphthenes in the product stream was equal to the level of ethylcyclohexane in the feed. The product stream was analysed by on-line GC for 10 h at a WHSV of 3.5 h$^{-1}$, and subsequently 4 h at a WHSV of 6.0 h$^{-1}$. From these data, the parameters in Table 1 were determined.

TABLE 1

| | | | | WHSV = 3.5 h$^{-1}$ | | WHSV = 6.0 h$^{-1}$ | |
|---|---|---|---|---|---|---|---|
| Shape | r | α | C/A$^a$ | EB conversion | pX-ATE | EB conversion | pX-ATE |
| CYL (comp) | 0.70 | — | 2.86 | 45.1 | 99.2 | 28.9 | 94.0 |
| TX (comp) | 0.51 | — | 2.72 | 42.3 | 98.7 | 27.0 | 91.6 |
| CYL | 0.50 | — | 4.0 | 46.1 | 100.1 | 29.9 | 96.8 |
| CYL | 0.20 | — | 10.0 | 48.1 | 100.6 | 32.1 | 98.5 |
| TL | 0.34 | 22 | 4.30 | 44.5 | 100.2 | 31.1 | 96.9 |
| QLSA | 0.36 | 22 | 3.42 | 41.2 | 100.1 | 27.7 | 96.9 |
| TX | 0.29 | — | 4.76 | 41.4 | 100.0 | 28.0 | 96.7 |
| TX | 0.26 | — | 5.44 | 41.8 | 100.0 | 28.4 | 97.1 |

$^a$Circumference (C)/area of the cross-section (A) of the extrudate.

The results shown in Table 1 unexpectedly demonstrate the pX-ATE values at both WHSV's tested increase significantly when the C/A ratio of the catalyst extrudates increases from 2.86 (comparative cylinders) or 2.72 (comparative TX shaped extrudates) to above 3. At the same time, ethylbenzene (EB) conversion is maintained at excellent levels.

The person skilled in the art will understand that the present invention can be carried out in many various ways without departing from the scope of the claims.

We claim:

1. A process for combined ethylbenzene reforming and xylene isomerisation, the process comprising:
    contacting a hydrocarbon feedstock comprising ethylbenzene and xylene with a catalyst to initiate the combined ethylbenzene reforming and xylene isomerization reactions,
        wherein said catalyst is the only catalyst present in the process and said catalyst comprises a catalyst carrier and one or more metals supported on the catalyst carrier, wherein the catalyst carrier is an extrudate comprising:
            (i) at least one of a ZSM-48 type zeolite and an EU-2 type zeolite; and
            (ii) an alumina binder, and
            wherein the extrudate has a shape with a C/A value of at least 3, where C is a circumference of the extrudate and A is a cross-sectional area of the extrudate.

2. The process according to claim 1, wherein a cross-section of the catalyst carrier has a shape selected from the group consisting of a circle, a trilobe, a quadralobe, and an extended trilobe.

3. The process according to claim 1, wherein a cross-section of the catalyst carrier has a shape selected from the group consisting of a trilobe, a quadralobe, and an extended trilobe.

4. The process according to claim 1 wherein the alumina binder is a wide-pore alumina having an average pore diameter of about 80 Å or greater.

5. The process according to claim 1 wherein the zeolite is present in an amount of from 30 to 70 wt % based upon the total weight of the catalyst.

6. The process according to claim 1 wherein the one or more metals supported on the catalyst carrier are selected from a Group VIII metal.

7. The process according to claim 6, wherein the Group VIII metal is present in an amount of from 0.1 to 3 wt %, based upon the total weight of the catalyst.

8. The process according to claim 7, wherein the Group VIII metal is present is an amount from 0.2 to 1 wt %, based upon the total weight of the catalyst.

9. The process according to claim 6, wherein the Group VIII metal is platinum.

* * * * *

UNITED STATES PATENT AND TRADEMARK OFFICE
CERTIFICATE OF CORRECTION

PATENT NO. : 11,673,847 B2
APPLICATION NO. : 17/416229
DATED : June 13, 2023
INVENTOR(S) : Erik Zuidema et al.

Page 1 of 1

It is certified that error appears in the above-identified patent and that said Letters Patent is hereby corrected as shown below:

In the Specification

In Column 7, Line 31, delete "QLI" and insert -- QLSA --.

In the Claims

In Column 10, Line 34, in Claim 8, delete "is" and insert -- in --.

In Column 10, Line 34, in Claim 8, delete "from" and insert -- of from --.

Signed and Sealed this
Sixteenth Day of July, 2024

Katherine Kelly Vidal
*Director of the United States Patent and Trademark Office*